United States Patent
Cline et al.

(10) Patent No.: US 6,281,681 B1
(45) Date of Patent: Aug. 28, 2001

(54) MAGNETIC RESONANCE IMAGING WITH INTERLEAVED FIBONACCI SPIRAL SCANNING

(75) Inventors: Harvey Ellis Cline; Thomas Richard Anthony, both of Schenectady, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/336,580

(22) Filed: Jun. 21, 1999

Related U.S. Application Data
(60) Provisional application No. 60/117,518, filed on Jan. 28, 1999.

(51) Int. Cl.$^7$ .............................. A61B 5/055; G01V 3/00
(52) U.S. Cl. ........................ 324/310; 324/309; 324/307
(58) Field of Search .................................... 324/309, 318, 324/310, 307; 378/87

(56) References Cited

U.S. PATENT DOCUMENTS

| | | | |
|---|---|---|---|
| Re. 32,712 | 7/1988 | Likes | 324/307 |
| 4,651,096 | 3/1987 | Buonocore | 324/309 |
| 4,731,583 | 3/1988 | Glover et al. | 324/309 |
| 4,748,410 | 5/1988 | Macovski | 324/309 |
| 4,992,736 | 2/1991 | Stormont et al. | 324/309 |
| 4,999,580 | 3/1991 | Meyer et al. | 324/309 |
| 5,233,301 | 8/1993 | Meyer et al. | 324/309 |
| 5,650,723 | 7/1997 | Meyer | 324/309 |
| 6,005,916 | * 12/1999 | Johnson et al. | 378/87 |

OTHER PUBLICATIONS

"Calculus Second Edition" a textbook by James Stewart, published by Brooks/cole publishing Company Pacific Grove, California 1991 pp. 566–569 of chapter 10 no month.*

* cited by examiner

Primary Examiner—Hezron Williams
Assistant Examiner—Tiffany A. Fetzner
(74) Attorney, Agent, or Firm—Jean K. Testa; Donald S. Ingraham

(57) ABSTRACT

An MRI system is employed to acquire image data using a pulse sequence in which k-space is sampled in a Fibonacci spiral trajectory. A single pulse sequence may be used to sample all of k-space with a single spiral arm, or k-space can be sampled with a plurality of interleaved Fibonacci spiral arms by performing a corresponding series of pulse sequences.

13 Claims, 3 Drawing Sheets

MAGNETIC RESONANCE IMAGING WITH INTERLEAVED FIBONACCI SPIRAL SCANNING

This application is related to Provisional Application U.S. Ser. No. 60/117,518 filed Jan. 28, 1999 in the U.S. Patent and Trademark Office, now abandoned, the contents of which are incorporated herein by reference, and the benefit of priority to which is claimed under 35 U.S.C. 119(e).

BACKGROUND OF THE INVENTION

This invention relates to nuclear magnetic resonance imaging methods and systems and, more particularly, to acquisition of images using spiral scanning methods.

When a substance such as human tissue is subjected to a uniform magnetic field (polarizing field $B_0$), the individual magnetic moments of the spins in the tissue attempt to align with this polarizing field along a longitudinal z axis, but precess about it in random order at their characteristic Larmor frequency. If the substance, or tissue, is subjected to a magnetic field (excitation field $B_1$) which is in the x-y plane and which is near the Larmor frequency, the net aligned moment $M_z$ may be rotated, or "tipped", into the x-y plane to produce a net transverse magnetic moment $M_t$. A nuclear magnetic resonance (NMR) signal is emitted by the excited spins after the excitation signal $B_1$ is terminated, and may be received and processed to form an image.

When utilizing NMR signals to produce images, magnetic field gradients ($G_x$ $G_y$ and $G_z$) are employed. Typically, the region to be imaged is scanned by a sequence of measurement cycles in which these gradients vary according to the particular localization method being used to sample a two or three dimensional region of k-space. The resulting set of received k-space signals is digitized and processed to reconstruct the image using one of many well known reconstruction techniques.

Most magnetic resonance (MR) scans currently used to produce medical images require many minutes to acquire the necessary k-space data. Reducing this scan time is an important objective, since a shortened scan increases patient throughput, improves patient comfort, and improves image quality by reducing motion artifacts. Reduction of scan time is particularly important in cardiac imaging, for example, where it is highly desirable to acquire sufficient NMR data to reconstruct an image in a single breath hold.

Many different pulse sequences are known in the art for acquiring NMR signals from which an image may be reconstructed. Most of these pulse sequences sample k-space in a rectilinear pattern, but there is a class of pulse sequences which sample k-space in a spiral pattern. It is known that a spiral sampling pattern can be achieved by applying a sinusoidally varying readout magnetic field gradient during acquisition of each NMR signal and that spiral scanning methods can be used to rapidly acquire NMR data from which an image may be reconstructed. A spiral scanning method is also known wherein the sinusoidal readout gradient is shaped to more rapidly traverse the spiral sampling trajectory and, therefore, more rapidly sample k-space data. Scan time has been further reduced in the past by acquiring samples from only one-half of k-space using interleaved spiral sampling trajectories.

Prior spiral trajectory k-space sampling methods are derived from Archimedian spirals of the form:

$$k_x(t)=a(t)\cos[a(t)]$$

$$k_y(t)=a(t)\sin[a(t)].$$

Given the amplitude and slew rate limitations of the gradient system hardware, the function a(t) is determined numerically such that k-space is sampled in a minimum scan time. While sampling with an Archimedian spiral trajectory allows very short scan times, the sampling of k-space is not uniform. The sampling is more dense near the center of k-space, with the result that the peripheral regions are undersampled if the central region is sampled at a rate needed to satisfy the Nyquist criteria. Such undersampling produces a variety of image artifacts in the reconstructed image.

SUMMARY OF THE INVENTION

Rapid acquisition of NMR image data from which an image can be reconstructed is achieved in an MRI system employing a predetermined pulse sequence to acquire NMR data that sample k-space in a Fibonacci spiral trajectory. The pulse sequence may be repeated to sample along a plurality of interleaved Fibonacci spiral trajectories, and if the number of interleaves is set equal to a number in a Fibonacci series, the total sampling is itself a Fibonacci spiral which samples substantially uniformly over k-space.

GENERAL DESCRIPTION OF THE INVENTION

Figure 1:
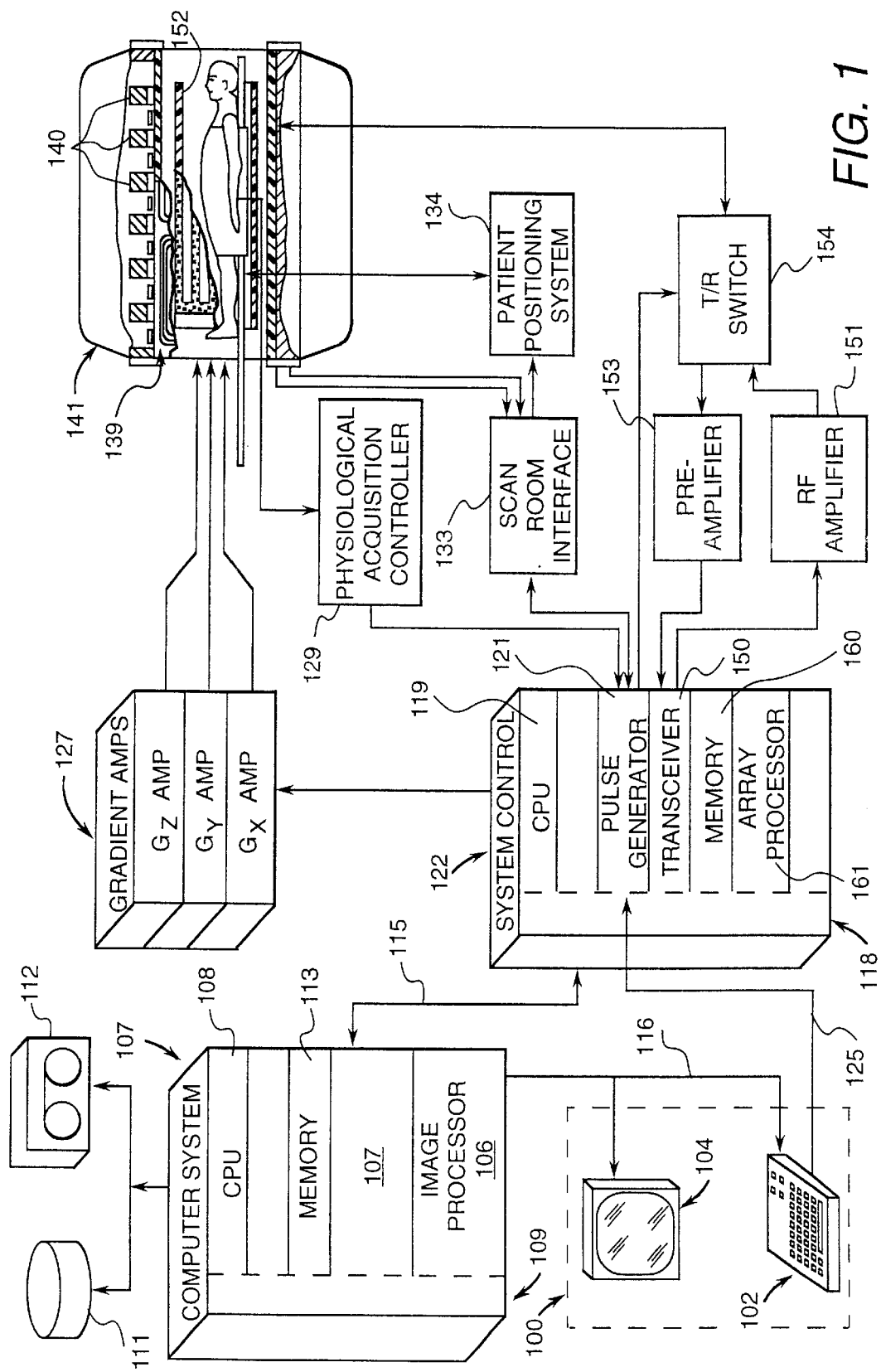
FIG. 1 is a block diagram of an MRI system employing the invention.

It has been observed in nature that seeds of the sunflower plant are arranged in a spiral pattern and that the seeds are uniformly spaced. This phenomenon has been explained using what is termed a "Fibonacci spiral". A Fibonacci series is derived from the recursive equation:

$$f(n+2)=f(n+1)+f(n), \quad (1)$$

where f(0)=1 and f(1)=1. The resulting series of Fibonacci numbers (i.e. 1, 2, 3, 5, 8, 13, 21, 34, 55, 89, 144, . . . ) has the property that the ratio of two successive numbers in the series (i.e. f(n)/f(n+1)) approaches a constant value:

$$F=(\sqrt{5}-1)/2 \quad (2)$$

A Fibonacci spiral is a spiral in which the angle about the origin between successive sample points is a fixed Fibonacci angle $\phi_F$:

$$\phi_F=2\pi(1-F)\approx 137.5 \text{ degrees.} \quad (3)$$

The Fibonacci spiral k-space sampling trajectory of the invention is of the form:

$$k_x(t)=r(t)\cos(\phi_F t)$$

$$k_y(t)=r(t)\sin(\phi_F t) \quad (4)$$

where: t=0, 1, 2, 3 . . . N,
 N=total number of samples, and
 r(t)=is a function that relates maximum gradient slew rate and maximum gradient amplitude to the velocity and acceleration of k-space sampling.

The readout gradient waveform amplitude needed to provide this sampling trajectory is related to the velocity at which the k-space Fibonacci spiral sampling trajectory is sampled by:

$$G_x(t)=(dk_x(t)/dt)/\gamma \quad (5)$$

$$G_y(t)=(dk_y(t)/dt)/\gamma.$$

The readout gradient waveform slew rate is related to the acceleration at which the k-space sampling trajectory is sampled by:

$$d(G_x(t)/dt=(d^2k_x(t)/dt)/\gamma \quad (6)$$

$$d(G_y(t)/dt=(d^2k_y(t)/dt)/\gamma.$$

Given the amplitude and slew rate limitations of the gradient system hardware, the function r(t) in equations (4) is determined numerically by solving the differential equation that relates the maximum gradient slew rate and maximum gradient amplitude to the velocity and acceleration of k-space sampling.

The optimal sampling of k-space using a spiral trajectory usually requires that a plurality of shorter, interleaved spiral acquisitions be performed. This enables the acquisition time of each pulse sequence to be reduced such that $T_2$ effects on the acquired NMR signals are kept to a minimum. This is accomplished with the Fibonacci spiral by creating a number (M) of spiral arms equal to one of the numbers in the Fibonacci series of equation (1). The Fibonacci spiral k-space trajectories of equation (4) are modified as follows for the jth spiral arm:

$$k_x(Mt+j)=r(Mt+j)\cos(\phi_F Mt+j)$$

$$k_x(Mt+j)=r(Mt+j)\sin(\phi_F Mt+j) \quad (7)$$

where: t=0, 1, 2, 3, . . . , N/M. The starting index j is incremented for each successive spiral arm. The starting angle of each successive spiral arm is incremented by an amount $2\pi/M$ and the resulting interleaved set of Fibonacci spiral trajectories produces a Fibonacci spiral trajectory in which k-space is sampled substantially uniformly throughout k-space. To obtain a uniform density of sample points, the function r(t) varies as the square root of time t. Since the square root function results in an infinite trajectory acceleration at the origin of k-space, the sampling trajectory speed is attenuated near the center of k-space. This is accomplished by taking a longer time to sample k-space near the origin.

Figure 3:
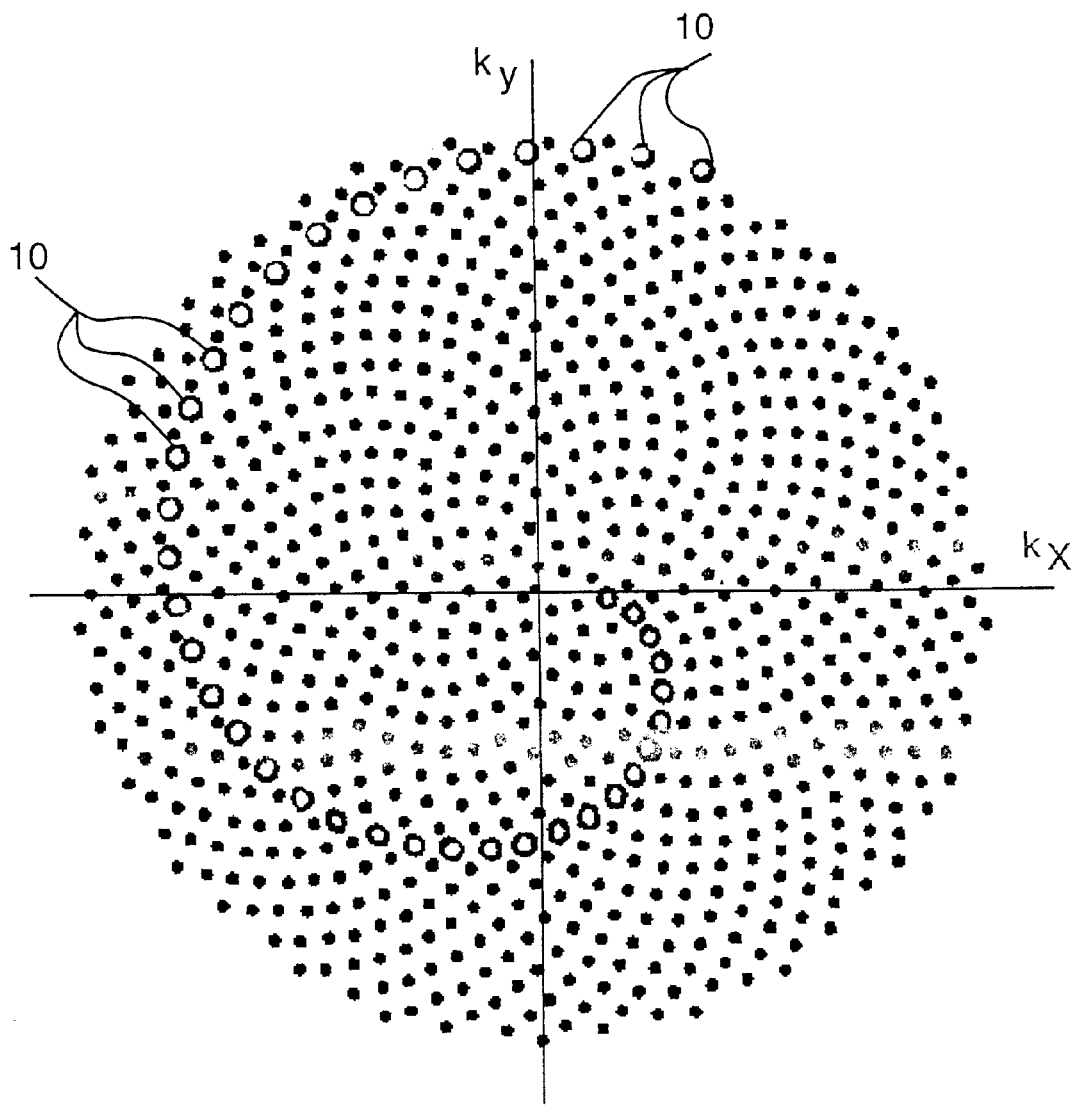
FIG. 3 is a graphic representation of the k-space sampling pattern performed by the pulse sequence of FIG. 2.

The Fibonacci spiral k-space sampling pattern is illustrated in FIG. 3. This particular pattern, which includes 804 sample points used to reconstruct a 32×32 pixel image, was acquired with M=21 separate Fibonacci spiral trajectories, one of which is illustrated by the sample points shown as circles 10. It is apparent from this illustration that the interleaved Fibonacci spiral sampling trajectories provide substantially uniform sampling throughout k-space.

DESCRIPTION OF THE PREFERRED EMBODIMENTS

FIG. 1 illustrates the major components of an MRI system which incorporates the invention. Operation of the system is controlled from an operator console 100 which includes a keyboard and control panel 102 and a display 104. Console 100 communicates through a link 116 with a separate computer system 107 that enables an operator to control the production and display of images on the screen of display 104. Computer system 107 includes several modules which communicate with each other through a backplane 109, including an image processor 106, a CPU 108 and a memory 113, known in the art as a frame buffer, for storing image data arrays. Computer system 107 is linked to a disk storage 111 and a tape drive 112 for storing image data and programs, and communicates with a separate system control 122 through a high speed serial link 115.

System control 122 includes a set of modules interconnected by a backplane 118, including a CPU 119 and a pulse generator 121 coupled to operator console 100 through a serial link 125. System control 122 receives, through link 125, operator commands which specify the scan sequence to be performed. Pulse generator module 121 operates the system components to carry out the desired scan sequence, and produces data which indicate the timing, strength and shape of the RF pulses to be produced, and the timing and length of the data acquisition window. Pulse generator module 121 is coupled to a set of gradient amplifiers 127 to control the timing and shape of the gradient pulses to be produced during the scan. Pulse generator 121 also receives patient data from a physiological acquisition controller 129 that receives signals from various sensors attached to the patient, such as electrocardiograph (ECG) signals from electrodes or respiratory signals from a bellows. Pulse generator module 121 is also coupled to a scan room interface circuit 133 which receives signals from various sensors associated with the condition of the patient and the magnet system. A patient positioning system 134 receives commands through scan room interface circuit 133 to move the patient to the desired position for the scan.

The gradient waveforms produced by pulse generator 121 are applied to gradient amplifier system 127 comprised of $G_x$, $G_y$ and $G_z$ amplifiers. Each gradient amplifier excites a corresponding gradient coil in an assembly 139 to produce the magnetic field gradients used for position encoding acquired signals. Gradient coil assembly 139 forms part of a magnet assembly 141 which includes a polarizing magnet 140 and a whole-body RF coil 152. Gradient amplifiers 127 are limited both in the peak current they can produce and the rate at which they can change current in gradient coils 139. As a result, the gradient field amplitude is limited, as is its slew rate.

A transceiver module 150 in system control 122 produces pulses which are amplified by an RF amplifier 151 and coupled to RF coil 152 by a transmit/receive switch 154. The resulting signals radiated by the excited nuclei in the patient may be sensed by the same RF coil 152 and supplied through transmit/receive switch 154 to a preamplifier 153. The amplified NMR signals are demodulated, filtered, and digitized in the receiver section of transceiver 150. Transmit/receive switch 154 is controlled by a signal from pulse generator 121 to electrically couple RF amplifier 151 to coil 152 during the transmit mode and to couple preamplifier 153 to coil 152 during the receive mode. Transmit/receive switch 154 also enables a separate RF coil (for example, a head coil or surface coil, not shown) to be used in either the transmit or receive mode.

The NMR signals picked up by RF coil 152 are digitized by transceiver 150 and transferred to a memory module 160 in system control 122. The receiver in transceiver 150 preserves the phase of the acquired NMR signals in addition to signal magnitude. The down converted NMR signal is applied to the input of an analog-to-digital (A/D) converter (not shown) which samples and digitizes the analog NMR signal. The samples are applied to a digital detector and signal processor which produces 16-bit in-phase (I) values and 16-bit quadrature (Q) values corresponding to the received NMR signal. The resulting stream of digitized I and Q values of the received NMR signal are supplied through backplane 118 to memory module 160 where they are employed to reconstruct an image. For a more detailed description of the receiver, reference is made to Stormont et al. U.S. Pat. No. 4,992,736, issued Feb. 12, 1991 and assigned to the instant assignee.

When the scan is completed and an entire array of k-space data has been acquired in memory module 160, an array processor 161 operates to Fourier transform the data into an array of image data which are conveyed through serial link 115 to computer system 107 to be stored in disk storage 111. In response to commands received from operator console 100, these image data may be archived on tape drive 112, or it may be further processed by image processor 106 and conveyed to operator console 100 for presentation on display 104.

Figure 2:
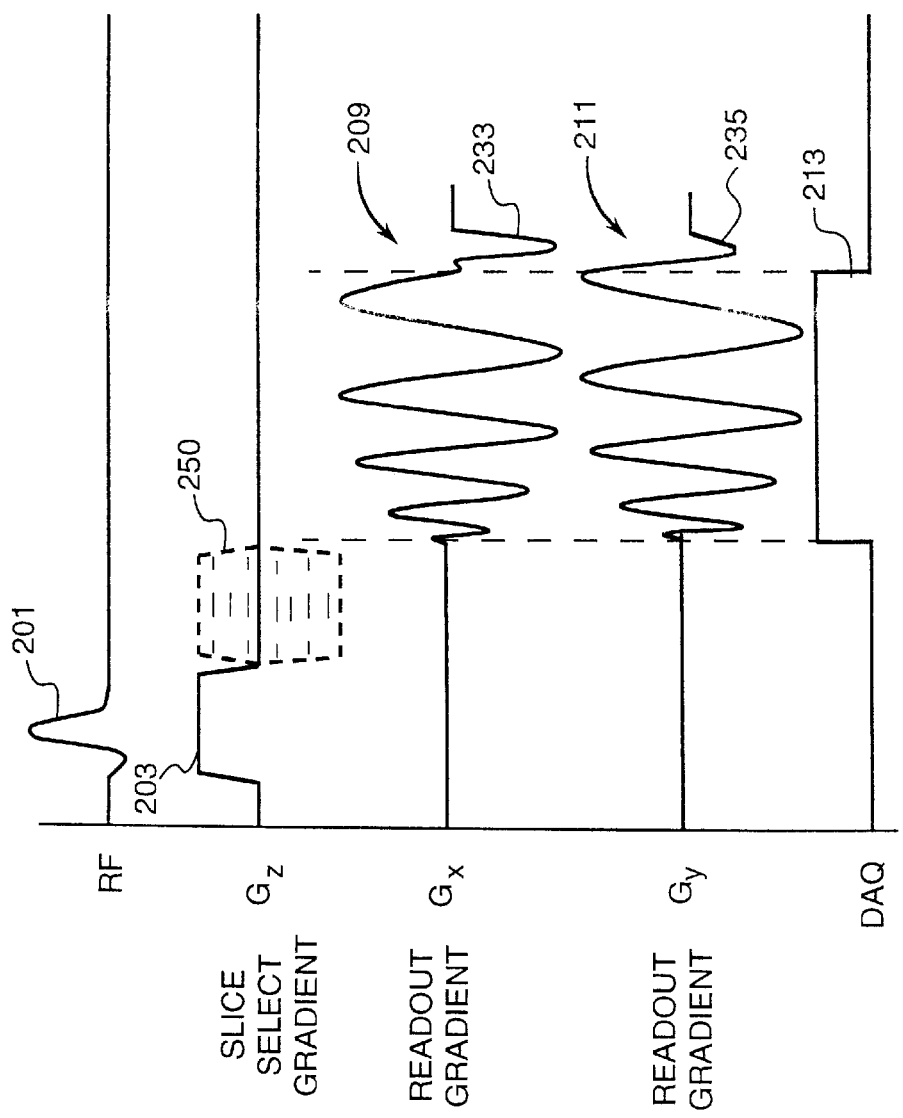
FIG. 2 is a graphic representation of a preferred pulse sequence for practicing/he invention.

The MRI system of FIG. 1 is employed to acquire NMR data using the pulse sequence of FIG. 2. This pulse sequence is performed under the direction of pulse generator module 121 (FIG. 1) which directs the system components to produce the indicated RF pulses and gradient waveforms.

The preferred pulse sequence, shown in FIG. 2, is two-dimensional, and includes a selective RF excitation pulse 201 that is produced in the presence of a $G_z$ slice select gradient pulse 203 to produce transverse magnetization in a selected slice of spins in the subject to be imaged. Sinusoidal readout gradient waveforms 209 and 211 that produce time varying magnetic field gradients along the respective $G_x$ and $G_y$ gradient axes are then produced. An NMR signal is acquired during an interval 213 to sample one Fibonacci spiral trajectory. Rephasing gradient pulses 233 and 235 are also applied during this interval after the respective readout gradient waveforms 209 and 211 to rephase the spin magnetization in preparation of the pulse sequence to follow. Each pulse sequence acquires one spiral arm of k-space samples such as the trajectory indicated by circles 10 in FIG. 3.

Readout gradient waveforms 209 and 211 are derived from equations (6) and (7) above, where the particular Fibonacci number of arms M is determined by the particular application. Each pulse sequence in the scan of M pulse sequences is substantially the same, except that sinusoidal readout gradient waveforms 209 and 211 are advanced in phase by an amount 2π/M to interleave the spiral arms and uniformly sample k-space as illustrated by the sample dots in FIG. 3. At the completion of the scan the acquired k-space data set is regrided into a rectilinear, two-dimensional array of k-space data using a well-known method. An image is reconstructed by performing a two-dimensional Fourier transformation on the regrided k-space data set.

As an example of use of the invention, consider an optimal Fibonacci spiral acquisition for an MRI system having a maximum gradient of 4 gauss/cm and a maximum slew rate of 15,000 gauss/cm/sec. The desired image resolution is 0.1 cm which sets the maximum size of k-space. For a 0.1 cm resolution the maximum value of the radial vector in k-space is 31.4 (1/cm). The spacing between the k-space sample points is inversely proportional to the field of view in real space. Since the spiral sampling creates a packed array of sample points that is more dense than a rectilinear array, the number of sample points may be reduced by a factor of 0.866. For a field of view of 12.8 cm the number of points required is 64*64*π*.866=8992. Using M=21 interleaved spiral arms, the duration of the spiral arm acquisition during each acquisition period 213 is 17 ms for a gradient of 3.9 gauss/cm and slew rate of 13,000 gauss/cm/sec. The total spiral acquisition time for acquiring all 21 Fibonacci spiral arms is 357 ms.

Many variations of the preferred embodiments are possible. For example, a three-dimensional image may be acquired by adding phase encoding in the slice select direction as indicated in FIG. 2 by dashed lines 250. For each separate $G_z$ phase encoding value, k-space is sampled using one or more spiral trajectories as described above. The process is repeated for each $G_z$ phase encoding value (e.g. 16 values) until a 3D k-space data set is acquired.

The invention may be used with pulse sequences other than those described herein. In addition, other RF excitation methods for producing transverse magnetization may be used, including spectral-spatial excitation. Moreover, one or more gradient axis may be flow compensated by the addition of gradient moment nulling pulses as described in Glover et al. U.S. Pat. No. 4,731,583, issued Mar. 15, 1988 and assigned to the instant assignee.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A method of employing a magnetic resonance imaging system to produce an image, comprising the steps of:
   a) producing a polarizing magnetic field in a subject to be imaged;
   b) generating an RF excitation pulse for producing transverse magnetization in the subject;
   c) sampling k-space in a Fibonacci spiral trajectory that extends from the center of k-space to the periphery of k-space by applying time-varying magnetic field gradients to the subject during an acquisition period;
   d) acquiring an NMR signal during the acquisition period; and
   e) reconstructing an image from the acquired NMR signal.

2. The method as recited in claim 1 including repeating steps b), c) and d) and performing step e) using all the acquired NMR signals.

3. The method as recited in claim 2 including sampling a plurality of interleaved Fibonacci spiral trajectories.

4. The method as recited in claim 3 wherein the number of interleaved Fibonacci spiral trajectories is equal to a number selected from a Fibonacci series of numbers.

5. The method as recited in claim 4 wherein the Fibonacci series is defined by the recursive equation:

$$f(n+2)=f(n+1)+f(n)$$

where: f(0)=1 and f(1)=1.

6. The method as recited in claim 1 wherein the time varying magnetic field gradients include two components $G_x(t)$ and $G_y(t)$ defined by the equations:

$$G_x(t)=dk_x(t)/dt/\gamma \text{ and}$$

$$G_y(t)=dk_y(t)/dt\times\gamma,$$

$$k_x(t)=r(t)\cos(\varphi ft);$$

$$k_y(t)=r(t)\sin(\varphi ft);$$

$\phi_F \approx 137.5$ degrees;

t is an integer from 0 to N; and

N is the total number of samples on a sampled Fibonacci spiral trajectory.

7. The method as recited in claim 6 including sampling of a plurality of interleaved Fibonacci spiral trajectories and wherein the number of interleaved Fibonacci spiral trajectories is selected from a Fibonacci series of numbers.

8. A magnetic resonance imaging (MRI) system comprising:

A) a magnet system that produces a polarizing magnetic field in a subject;

B) an RF excitation pulse generator that produces transverse magnetization in the subject;

C) a magnetic field gradient assembly that applies time varying magnetic field gradients which sample k-space in a Fibonacci spiral trajectory extending from the center of k-space to the periphery of k-space, during an acquisition period;

D) a receiver that acquires an NMR signal during the acquisition period; and

E) an array processor that transforms the acquired NMR signal into an array of image data.

9. The magnetic resonance imaging system as recited in claim 8, further including a pulse generator for controlling the RF excitation pulse generator, the magnetic field gradient assembly and the receiver, whereby the NMR signal is acquired by performing a single pulse sequence.

10. The magnetic resonance imaging system as recited in claim 9 wherein the pulse generator is operable to repeat the pulse sequence a plurality of times to acquire a plurality of NMR signals, and the array processor for transforming the acquired NMR signal into an image that employs all the acquired NMR signals.

11. The magnetic resonance imaging system of claim 10 wherein the number of times the pulse sequence is performed is selected from a Fibonacci series of numbers.

12. The magnetic resonance imaging system as recited in claim 11 wherein the Fibonacci series is defined by the recursive equation:

$$fg(n+2)=f(n+1)+f(n)$$

where $f(0)=1$ and $f(1)=1$.

13. The magnetic resonance imaging system as recited in claim 8 wherein the time varying magnetic field gradients include two components ($G_x(t)$ and $G_y(t)$) defined by the equations:

$$G_x(t)=dk_x(t)/dt/\gamma \text{ and}$$

$$G_y(t)=dk_y(t)/dt\times\gamma,$$

$$k_x(t)=r(t)\cos(\phi ft);$$

$$k_y(t)=r(t)\sin(\phi ft);$$

$\phi_F \approx 137.5$ degrees;

t is an integer from 0 to N; and

N is the total number of samples on a sampled Fibonacci spiral trajectory.

* * * * *